United States Patent [19]
Sugiya et al.

[11] Patent Number: 5,892,120
[45] Date of Patent: Apr. 6, 1999

[54] HIGHLY PURE MONOALKYLPHOSPHINE AND METHOD FOR PRODUCING SAME

[75] Inventors: Masashi Sugiya; Tsutomu Watanabe; Natsuhiro Sano, all of Tokyo, Japan

[73] Assignees: Nippon Chemical Industrial Co., Ltd.; Shin-Etsu Chemical Co., Ltd., both of Tokyo, Japan

[21] Appl. No.: 977,807

[22] Filed: Nov. 25, 1997

[30] Foreign Application Priority Data

Nov. 29, 1996 [JP] Japan .................................. 8-320051

[51] Int. Cl.⁶ ...................................................... C07F 9/52
[52] U.S. Cl. .................................................................. 568/8
[58] Field of Search ...................................... 568/8

[56] References Cited

U.S. PATENT DOCUMENTS

| 2,584,112 | 2/1952 | Brown . | |
| 5,260,485 | 11/1993 | Calbick | 568/8 |
| 5,284,977 | 2/1994 | Imori | 568/8 |
| 5,354,918 | 10/1994 | Ohsaki | 568/8 |

*Primary Examiner*—Gary Geist
*Assistant Examiner*—Jean F Vollano
*Attorney, Agent, or Firm*—Wenderoth, Lind & Ponack, L.L.P.

[57] ABSTRACT

A highly pure monoalkylphosphine which is useful as a starting material for producing a compound semiconductor, and a method for producing same in high yield are provided. A highly pure monoalkylphosphine represented by the general formula $RPH_2$ (wherein R is an alkyl group having 1 to 8 carbon atoms) has a purity of not less than five nines, and is substantially free of sulfur and silica. In the method of producing said highly pure monoalkylphosphine, anhydrous hydrofluoric acid is used as a catalyst for a reaction between phosphine and an alkene, and the reaction is carried out in the presence of an organic solvent having a boiling point higher than that of the resulting monoalkylphosphine; the resulting reaction mixture is contacted with an alkali solution so that the remaining catalyst is removed into an aqueous phase in the form of a fluoride salt; next, the obtained reaction mixture is contacted with an alkali hydride and the impurities are removed, then distillation is carried out.

4 Claims, No Drawings

HIGHLY PURE MONOALKYLPHOSPHINE AND METHOD FOR PRODUCING SAME

BACKGROUND OF THE INVENTION

1. Field of the Invention

The present invention relates to a highly pure monoalkylphosphine which is useful as a starting material for use in epitaxial growth by a Metal Organic Chemical Vapor Deposition (MOCVD) method and the like, and a method for producing same. More specifically, the present invention relates to a highly pure monoalkylphosphine which is substantially free of sulfur or silica, and a method for producing same.

2. Description of the Related Art

Recently, compound semiconductors have been widely used in various fields such as light emitting diodes, semiconductor lasers, and high electron mobility transistors (HEMT). An epitaxial crystal-growth technique, such as a Metal Organic Chemical Vapor Deposition (MOCVD) method, has often been used as a method for preparing compound semiconductors. Compound semiconductors produced by such an epitaxial crystal-growth technique include Group III–V compound semiconductors, and phosphine which contains phosphorus atom is used as a source of Group V elements.

However, phosphine has a safety problem since it is highly toxic and is in a gaseous form at ordinary temperatures. Accordingly, when phosphine is used for producing a compound semiconductor, it is necessary to use it under high pressure.

Recently, use of monoalkylphosphine in place of conventional phosphine has been proposed in order to avoid the dangers associated with phosphine. Although it is not desirable for the epitaxial growth film to contain carbon as an impurity, monoalkylphosphine allows only a small amount of carbon to be mixed in the epitaxial growth film, and it has a lower toxicity than phosphine; thus, monoalkylphosphine has been catching attention as a substitute for phosphine.

As methods for preparing monoalkylphosphines, there have been known, for instance, those comprising reducing phosphonium chloride and phosphonous acid, such as described in Z. anorg. allg. Chem. 433, 42 (1978) and the like. Japanese Patent Laid-Open Nos.4-9392 and 4-9391 disclose methods in which phosphonium chloride is produced by the Grignard method or the Friedel-Crafts method respectively, and is reduced by the use of a reducing agent such as lithium aluminium hydride to give a monoalkylphosphine.

In these methods, it is very difficult to obtain a highly pure monoalkylphosphine since the metallic reducing agents used for the reduction reaction, a magnesium compound in the Grignard method and an aluminium compound in the Friedel-Crafts method, tend to become included as metal impurities. In addition, the production processes are multi-stage processes which result in decreased yield and disadvantages in the practice thereof on an industrial scale.

In the specification of U.S. Pat. No. 5,354,918, it is described that an alkanesulfonic acid, such as methanesulfonic acid, is used as a catalyst to produce phosphine and olefin. In this patent, the methanesulfonic acid catalyst used is mixed in an organic solvent containing monoalkylphosphine. Thus a step to remove the catalyst, comprising, for example, washing with an alkali aqueous solution such as sodium hydroxide aqueous solution, becomes necessary. Nevertheless, even after such procedures are carried out repeatedly, a trace amount of methanesulfonic acid remains and it is difficult to remove the methanesulfonic acid completely by subsequent purification processes such as distillation and precision distillation.

If a trace amount of sulfur or silica is mixed in the monoalkylphosphine, the carrier concentration of the compound semiconductor formed from crystals prepared through the epitaxial growth of the monoalkylphosphine is lowered, and the product cannot be used for applications requiring a high purity, such as an embedded laser.

SUMMARY OF THE INVENTION

Therefore, an object of the present invention is to provide a highly pure monoalkylphosphine which is useful as a starting material for producing a compound semiconductor, and a method for producing the highly pure monoalkylphosphine in high yield.

The present inventors have carried out an extensive study and solved the above-mentioned conventional problems.

Accordingly, an object of the present invention is to provide a highly pure monoalkylphosphine which is represented by the general formula $RPH_2$ (wherein R is an alkyl group having 1 to 8 carbon atoms) the purity of which is not less than 99.999% (five nines), and which is substantially free of sulfur and silica.

Another object of the present invention is to provide said highly pure monoalkylphosphine, wherein the monoalkylphosphine is mono-1,1-dimethylethylphosphine which is used as a starting material for a compound semiconductor.

Still another object of the present invention is to provide a method for producing a highly pure monoalkylphosphine containing a step in which phosphine and an alkene are allowed to react, which comprises:

step 1) in which anhydrous hydrofluoric acid is used as a reaction catalyst and the reaction is carried out in the presence of an organic solvent having a boiling point higher than that of the resulting monoalkylphosphine;

step 2) in which the resulting reaction mixture is contacted with an alkali solution and the remaining catalyst is removed in the aqueous phase as a fluoride salt; and step 3) in which the reaction solution obtained in step 2 is contacted with an alkali hydride to remove impurities, then distillation is carried out.

A further object of the present invention is to provide said method for producing a highly pure monoalkylphosphine, wherein the alkali solution is an aqueous solution of a hydroxide of a Group Ia metal or Group IIa metal, or an aqueous solution of ammonia or an amine type compound.

A still further object of the present invention is to provide said method for producing a highly pure monoalkylphosphine, wherein the Group Ia metal is sodium or potassium.

A yet still further object of the present invention is to provide said method for producing a highly pure monoalkylphosphine, wherein the alkali hydride is at least one substance selected from the group consisting of sodium hydride, aluminium lithium hydride and calcium hydride.

DETAILED DESCRIPTION OF THE INVENTION

The present invention will be further explained in detail.

The highly pure monoalkylphosphine of the present invention can be represented by the general formula $RPH_2$. In the formula, R represents an alkyl group having 1 to 8 carbon atoms, such as isopropyl group, tert-butyl group, tert-amyl group, and tert-octyl group, but the tert-butyl group is particularly preferable.

The monoalkylphosphine is highly pure, having a purity of not less than five nines, and substantially free of sulfur and silica.

The phrase "substantially free of-sulfur and silica," means that the content of sulfur and silica are below the detection limits when measuring by an ICP-atomic emission spectroscopy method. "Below the detection limit," means the values are not more than 10 ppb respectively.

In one preferred embodiment of the present invention, the highly pure monoalkylphosphine of the present invention is mono-1,1-dimethylethylphosphine which is particularly preferable as a starting material for a compound semiconductor.

The method of the present invention will be more concretely explained.

Phosphine, which is the starting material used in the first step of the present invention, can be produced by any production method, but it is preferable to use a product of a high purity which contains very little metallic and oxidative impurities. Industrially advantageous and preferable is, for example, purified phosphine which is obtained from crude phosphine by-produced in a soda hypophosphite production process, subjected to an arsine removal process or lower phosphorus hydride compound removal process, followed by precision distillation in a distilling apparatus so that it becomes substantially free of impurities such as low boiling point components, $CO_2$, $H_2O$, and arsine.

Alkenes, which are used as another starting material, are unsaturated aliphatic hydrocarbons having a straight or branched chain, and those having 1 to 8 carbon atoms are preferable. Examples thereof include isobutene, 2-methyl-1-butene, 2-ethyl-1-butene, 2-methyl-1-pentene, 2-methyl-1-hexene, 2,3,3-trimethyl-1-butene, 2,3-dimethyl-1-hexene, 2-ethyl-1-hexene, isooctene, 2-methyl-1-heptene, 2,2,4-trimethyl-1-pentene, 2,4-dimethyl-1-hexene, 2,4,4-trimethyl-1-hexene and the like.

One of the features of step 1 of the present invention is that anhydrous hydrofluoric acid is used as the catalyst in the reaction between the above-mentioned compounds.

Another important feature of step 1 is that a solvent having a boiling point higher than that of the resulting monoalkylphosphine is employed as the reaction solvent. This is because the difference in boiling points is utilized to remove the highly pure monoalkylphosphine from the reaction solvent by distillation or, if necessary, precision distillation, which is carried out after the completion of the reaction. As the reaction solvent, saturated aliphatic hydrocarbons are suitable, and in particular, saturated aliphatic hydrocarbons having 8 to 18 carbon atoms are preferable. Examples include n-octane, isooctane, n-nonane, n-decane, n-tridecane, n-tetradecane, n-hexadecane, n-octadecane and the like. Mixed solvents such as n-paraffin can be used as well.

The other feature of step I of the present invention is that the above-mentioned reaction is carried out in a water-free system. By carrying out the reaction in a water-free system, the generation of secondary or tertiary alkylphosphine compounds, which are inevitably by-produced in an aqueous system, can be controlled.

The reaction conditions vary depending on the physical properties of the starting materials, the solvent, and the catalyst selected, but as an example, reaction is carried out under pressure (for example a gauge pressure of 10–30 kg/cm$^3$) in a high pressure vessel such as an autoclave, an alkene/phosphine molar ratio of from 1:1 to 1:5, preferably 1:1 to 1:2.5. The amount of the catalyst to be added can be decided appropriately, and in an illustrative example for an alkene, it is from 0.1 to 2.0 moles, preferably 0.5 to 1.5 moles. The reaction temperature is between room temperature and 100° C., preferably between 20° and 40° C., and the reaction time is normally from 1 to 24 hours, preferably 2 to 10 hours.

The introduction of the starting materials can be favorably carried out by introducing a reaction solvent into a reaction vessel such as an autoclave, sufficiently replacing the atmosphere in the reaction vessel with an inactive gas such as nitrogen and helium, and introducing a reaction catalyst then phosphine into the reaction vessel under pressure while the reaction vessel temperature is lowered to as low as about $-1°$ C. Further, it is desirable that an alkene dissolved in the reaction solvent or an alkene alone be introduced into another autoclave, pressurized using an inactive gas such as nitrogen, then gradually introduced under pressure into the reaction vessel containing the phosphine.

After the reaction is completed and the reaction vessel is cooled down to room temperature, the excess amount of unreacted phosphine is replaced with an inactive gas followed by allowing the reaction solution to stand for about 24 hours.

Next, step 2 is a step in which unreacted anhydrous hydrofluoric acid remaining in the reaction solution is removed by being brought into contact with an alkali solution.

Examples of the alkali solution to be used include an aqueous solution of a hydroxide of Group Ia metals, Group IIa metals, and ammonia or amine type compounds.

The concentration of the aqueous solution is preferably from 0.1 to 3N. The amine type compounds hereby include aliphatic amine compounds substituted with an alkyl group having up to 4 carbon atoms, urea and tetramethyl urea, i.e. a derivative of urea. These alkali solutions can be used alone or in combination. Among them, aqueous solutions of hydroxides of Group Ia metals, preferably sodium and potassium, having concentrations ranging from 0.5 to 2N are particularly preferable. For preparation of the aqueous solution, an alkali compound of high purity is preferably dissolved in extra-pure water.

After addition of the alkali solution, the reaction solution is stirred at a normal temperature or under heating. The amount of the alkali solution added is 1.0–3.0 moles, preferably 1.1–1.5 moles per 1 mole of hydrofluoric acid used as the catalyst. By such a process, the anhydrous hydrofluoric acid used as the catalyst can be sufficiently removed.

Next, step 3 is a step in which the reaction solution treated in the previous step is brought into contact with an alkali hydride to remove impurities, and distillation is carried out.

Examples of the alkali hydride to be used include sodium hydride, aluminium lithium hydride or calcium hydride.

The contact is preferably carried out by adding an alkali hydride to the reaction solution followed by reflux treatment in an inactive gas atmosphere such as nitrogen or argon. By this treatment, impurities such as water and alcohol can be removed.

Then the reaction solution (organic phase) after the treatment is subjected to simple distillation under a normal pressure and, if necessary, further purified by precision distillation to give a highly pure monoalkylphosphine which is free of impurities.

The addition of an alkali solution, the stirring, the treatment with the alkali hydride, and the distillation steps can be repeatedly carried out.

Since neither sulfur compounds nor silicon compounds are used in the reaction according to the present invention, a monoalkylphosphine of extremely high purity can be obtained, because sulfur and silica, which are said to degrade the quality of crystal growth, are not contained in the monoalkylphosphine.

The present invention improves the conventional method of producing a monoalkylphosphine wherein phosphine and an alkene are allowed to react, and the method of the present invention allows a highly selective and highly pure monoalkylphosphine which is free from sulfur and silica impurities to be advantagously produced industrially. The monoalkylphosphine obtained according to the present invention can be effectively utilized as a source of phosphorus, a Group V element for a compound semiconductor.

EXAMPLES

The present invention will hereinafter be described in more detail in the following Examples.

Example 1

Into a stainless autoclave having a capacity of about 10 liters (first autoclave), was added 2 liters of n-paraffin SL (produced by Nippon Petrochemical Co., Ltd.) as a solvent. Then, the vessel was purged by thoroughly replacing the atmosphere therein with nitrogen and then a vacuum. Next, a bomb of anhydrous hydrofluoric acid was prepared in a hot bath of 35° C. and the first autoclave, while being cooled to −10° C. with cold brine, was charged with 200 g of the anhydrous hydrofluoric acid (10 moles) from the bomb. Then, the first autoclave, while being cooled with cold brine, was further charged with 952 g (28 moles) of purified phosphine gas which was by-produced in a soda phosphite production process. The pressure level as shown by the pressure gage of the first autoclave, rose to 22 kg/cm². Next, the first autoclave was heated with hot water to 40° C.

A separate autoclave having a capacity of about 5 liters (second autoclave) was charged with 2 liters of a solvent, n-paraffin SL (produced by Nippon Petrochemical Co., Ltd.) and 560 g (10 moles) of isobutylene. Then, after they were dissolved, the inner pressure of the second autoclave was raised to 30 kg/cm² using nitrogen. Next, isobutylene solution was gradually introduced into the first autoclave under pressure over 1 hour by adjusting the valve. The pressure in the first autoclave was reduced to 27–18 kg/cm2. Then the reaction mixture in the first autoclave was matured at 40° C. for 3 hours.

A neutralization bath having a capacity of 20 liters and a stainless agitator was charged with 12 liters of 1N sodium hydroxide aqueous solution, then cooled to 10° C. or less using an ice bath. The reaction mixture in the first autoclave was gradually added to the neutralization bath under stirring, and the hydrofluoric acid, used as the catalyst, was neutralized. After the reaction product was withdrawn, it was allowed to stand at room temperature over an entire day. Next, a separated lower phase comprising a sodium fluoride aqueous solution was removed, and the organic phase was further washed with 10 liters of 1N sodium hydroxide aqueous solution.

The obtained organic phase was analyzed by gas chromatography and 382.9 g of mono-1,1-dimethylethylphosphine was obtained (conversion rate: 42.5% on the basis of isobutylene).

To the organic phase, was added 20 g of calcium hydride and it was refluxed under a nitrogen atmosphere for 3 hours, then distilled at a normal pressure to give 350.0 g of a distillate having a mono-1,1-dimethylethylphosphine content of 93%. This was subjected to precision distillation at a normal pressure using a 15-stage Aldershow glass precision distillatory, and 245.9 g (yield: 27.3%) of mono-1,1-dimethylethylphosphine (boiling point: 54° C.) was isolated which had a purity of at least 99.999% according to the analytical results of gas chromatography.

An InP epitaxial film (Fe dope, film thickness of 5 μm) was grown under a normal pressure on an InP substrate from the obtained mono-1,1-dimethylethylphosphine and from commercially available highly pure trimethyl indium using a horizontal MOCVD apparatus. The crystal growth was carried out at 580° C., and at V/III ratio of 50. The electrical characteristics of the obtained epitaxial film were measured and;

the carrier concentration was n77 k=2–3×10$^{14}$ cm$^{-3}$; the surface homology was also very good.

The purity of the product obtained by relative area ratio as measured by gas chromatography (FID detector) was 99.999% or higher, and the amounts of sulfur and silica measured by ICP-atomic emission spectroscopy were below the detection limit (not more than 10 ppb).

Comparative Example 1

Into a stainless autoclave having a capacity of about 10 liters, were added 100 g of n-decane (boiling point: 174° C.), 80 g of isobutylene (1.426 mole) and 135.8 g (3.994 moles) of highly pure phosphine at room temperature. The pressure of the autoclave was 25 kg/cm². The reaction temperature was raised to 60° C. and 137 g (1.426 mole) of methanesulfonic acid purified by simple distillation was added thereto over about 1 hour by pressure pump. The pressure inside the autoclave was lowered from 35 kg/cm² down to 28 kg/cm². Again, the reaction mixture was kept at 60° C. for 1 hour and matured.

After the reaction was completed, the reaction mixture was cooled to about 30° C., the excess unreacted phosphine was removed through evacuation, and the atmosphere of the system was thoroughly replaced with nitrogen. The reaction product was allowed to stand at room temperature for an entire day, and then liquid-liquid separation was carried out and the lower phase comprising methanesulfonic acid was removed.

Next, 150 g of 1N sodium hydroxide aqueous solution was added thereto and stirred for 1 hour, allowed to stand, and liquid-liquid separation was carried out.

The obtained n-decane phase was analyzed by gas chromatography and it was found that 56.1 g of mono-1,1-dimethylethylphosphine (conversion rate: 43.7% on the basis of isobutylene) was obtained.

To this n-decane phase, was added 5 g of calcium hydride and the mixture was refluxed under a nitrogen atmosphere for 3 hours in a manner analogous to that used in Example 1; then distillation at a normal pressure was carried out, followed by precision distillation at a normal pressure, and 33.6 g (yield: 26.2%) of mono-1,1-dimethylethylphosphine (boiling point: 54° C.) having a purity of 99.99% or higher, measured by gas chromatography, was isolated.

InP epitaxial film was grown under a normal pressure on an InP substrate using a MOCVD apparatus similar to that used in Example 1, and the electric characteristics were measured and;

the carrier concentration was n77 k=0.8–1.0×10$^{15}$ cm$^{-3}$.

The purity of the product obtained by relative area ratio measured by gas chromatography (FID detector) was 99.99%, and the amounts of sulfur and silica measured by ICP-atomic emission spectroscopy were, sulfur: 150 ppb, and silica: 80 ppb.

While the invention has been described in detail and with reference to specific embodiments thereof, it will be apparent to one of ordinary skill in the art that various changes and modifications can be made therein without departing from the spirit and scope thereof.

What is claimed is:

1. A method for producing a monoalkylphosphine containing a step in which phosphine and an alkene are allowed to react, which comprises:

step 1) in which anhydrous hydrofluoric acid is used as a reaction catalyst and the reaction is carried out in the presence of an organic solvent having a boiling point higher than that of resulting monoalkylphosphine;

step 2) in which the resulting reaction mixture is contacted with an alkali solution and the remaining catalyst is removed in the aqueous phase as a fluoride salt; and step 3) in which the reaction solution obtained in the step 2) is contacted with an alkali hydride to remove impurities, and then distillation is carried out.

2. A method for producing a highly pure monoalkylphosphine according to claim 1, wherein the alkali solution is an aqueous solution of a hydroxide of a Group Ia metal or Group IIa metal, or an aqueous solution of ammonia or an amine type compound.

3. A method for producing a highly pure monoalkylphosphine according to claim 2, wherein the Group Ia metal is sodium or potassium.

4. A method for producing a highly pure monoalkylphosphine according to claim 1, wherein the alkali hydride is at least one substance selected from the group consisting of sodium hydride, aluminium lithium hydride and calcium hydride.

* * * * *